United States Patent [19]

Gasc et al.

[11] Patent Number: 4,591,589
[45] Date of Patent: May 27, 1986

[54] 2-ARYL PYRAZOLO[4,3-C]CINNOLIN-3-ONES

[75] Inventors: Jean-Claude Gasc, Bondy; Daniel Humbert, Fontenay-sous-Bois; Peter F. Hunt, Gonesse, all of France

[73] Assignee: Roussel Uclaf, Paris, France

[21] Appl. No.: 692,030

[22] Filed: Jan. 16, 1985

[51] Int. Cl.⁴ .................. A61K 31/50; C07D 487/02
[52] U.S. Cl. .................. 514/248; 544/234; 544/235
[58] Field of Search ............ 544/236, 234; 514/248; 546/82

[56] References Cited

U.S. PATENT DOCUMENTS

| | | | |
|---|---|---|---|
| 4,230,705 | 10/1980 | Allen, Jr. et al. | 514/248 |
| 4,260,755 | 4/1981 | Moran et al. | 544/236 |
| 4,312,870 | 1/1982 | Yokoyama | 546/82 |
| 4,464,372 | 8/1984 | Bristol et al. | 544/236 |
| 4,524,146 | 6/1985 | Yokoyama | 546/82 |

Primary Examiner—Donald G. Daus
Assistant Examiner—Stephen M. Kapner
Attorney, Agent, or Firm—Bierman, Peroff & Muserlian

[57] ABSTRACT

Novel pyrazolo[4,3-c]cinnolin-3-one derivatives of the formula

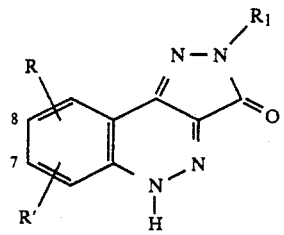

wherein R may be in the 7- or 8-position and is selected from the group consisting of hydrogen, halogen, alkyl and alkoxy of 1 to 5 carbon atoms, $-NO_2$ and $-CF_3$ and R' is hydrogen or R and R' taken together form an alkylenedioxy of 1 to 4 carbon atoms at the 7- or 8-positions and $R_1$ is selected from the group consisting of phenyl, pyridyl, thiazolyl, dihydrothiazolyl and thienyl, all optionally substituted with at least one member of the group consisting of alkyl and alkoxy of 1 to 5 carbon atoms, halogen, mono-, di- and tri- halomethyl and aralkoxy of 7 to 12 carbon atoms and their non-toxic, pharmaceutically acceptable acid addition salts having anxiolytic properties and novel intermediates therefore.

18 Claims, No Drawings

2-ARYL PYRAZOLO[4,3-C]CINNOLIN-3-ONES

STATE OF THE ART

Barker et al [*J. Chem. Soc.*, Vol. 61 (1961), p. 2828 to 2843] describe a cinnoline synthesis by cyclization of mesoxalyl chloride phenylhydrazones. Ames et al [*J. Chem. Soc.*, Supp. 1 (1964), p. 5659 to 5662] describe the reaction of methyl iodide and alkyl 6-chloro-4-substituted-cinnolin-3-ones. EPO patent No. 22,078 describes 2-aryl-pyrazolo[4,3-c]chinolin-3-(1 and 5H)-one derivatives.

OBJECTS OF THE INVENTION

It is an object of the invention to provide the novel pyrazolo[4,3-c]cinnolin-3-ones of formula I and their non-toxic, pharmaceutically acceptable acid addition salts and a novel process and intermediates for their preparation.

It is another object of the invention to provide novel anxiolytic compositions and a novel method of relieving anxiety in warm-blooded animals.

These and other objects and advantages of the invention will become obvious from the following detailed description.

THE INVENTION

The novel compounds of the invention are selected from the group consisting of pyrazolo[4,3-c]cinnolin-3-one derivatives of the formula

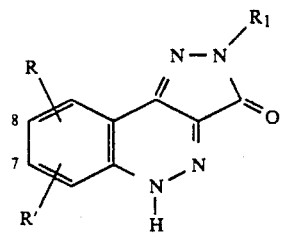

I wherein R may be in the 7- or 8-position and is selected from the group consisting of hydrogen, halogen, alkyl and alkoxy of 1 to 5 carbon atoms, —NO$_2$ and —CF$_3$ and R' is hydrogen or R and R' taken together form an alkylenedioxy of 1 to 4 carbon atoms at the 7- or 8-positions and R$_1$ is selected from the group consisting of phenyl, pyridyl, thiazolyl, dihydrothiazolyl and thienyl, all optionally substituted with at least one member of the group consisting of alkyl and alkoxy of 1 to 5 carbon atoms, halogen, mono-, di- and tri- halomethyl and aralkoxy of 7 to 12 carbon atoms and their non-toxic, pharmaceutically acceptable acid addition salts.

Examples of R are halogens such as bromine, iodine and preferably chlorine; alkyl such as methyl, ethyl, n-propyl, n-butyl, n-pentyl, isopropyl and isobutyl; alkoxy such as methoxy, ethoxy, propoxy, butoxy, pentoxy, isopropoxy; mono-, di-, and tri-halomethyl such as bromomethyl, chloromethyl, dichloromethyl, trifluoromethyl; aralkoxy such as naphthylmethoxy and preferably benzyloxy. When R and R' form an alkylenedioxy, it may be propylenedioxy, butylenedioxy and preferably methylenedioxy or ethylenedioxy.

Examples of suitable acids for the formation of the non-toxic, pharmaceutically acceptable acid addition salts are inorganic acids such as hydrochloric acid, hydrobromic acid, nitric acid, sulfuric acid and phosphoric acid and organic acids such as acetic acid, formic acid, propionic acid, benzoic acid, maleic acid, fumaric acid, succinic acid, tartaric acid, citric acid, oxalic acid, glyoxylic acid, aspartic acid, alkane sulfonic acids such as methane sulfonic acid and ethane sulfonic acid, aryl sulfonic acids such as benzenesulfonic acid and p-toluene sulfonic acid and arylcarboxylic acids.

Among the preferred compounds of formula I are those wherein R is hydrogen, halogen, alkyl and alkoxy of 1 to 5 carbon atoms, —NO$_2$ or —CF$_3$, those wherein R' is hydrogen, those wherein R$_1$ is phenyl optionally substituted with alkyl or alkoxy of 1 to 5 carbon atoms or halogen or R$_1$ is pyridyl or thiazolyl and their non-toxic, pharmaceutically acceptable acid addition salts. More preferably, R is in the 8-position and R$_1$ is phenyl and their acid addition salts.

Examples of preferred compounds of formula I are 8-chloro-2,5-dihydro-2-phenyl-3H-pyrazolo[4,3-c]cinnolin-3-one, 2,5-dihydro-2-phenyl-3H-pyrazolo[4,3-c]cinnolin-3-one, 2,5-dihydro-2-pyrid-2-yl-3H-pyrazolo[4,3-c]cinnolin-3-one, 2,5-dihydro-2-pyrid-3-yl-3H-pyrazolo[4,3-c]cinnolin-3-one, 2,5-dihydro-2-pyrid-4-yl-3H-pyrazolo[4,3-c]cinnolin-3-one, 2-(4-chlorophenyl)-2,5-dihydro-3H-pyrazolo[4,3-c]cinnolin-3-one, 2,5-dihydro-8-methoxy-(2-phenyl-3H-pyrazolo[4,3-c]cinnolin-3-one, 2,5-dihydro-8-methoxy-2-pyrid-2-yl-3H-pyrazolo[4,3-c]cinnolin-3-one, 2,5-dihydro-7,8-methylenedioxy-2-pyrid-2-yl-3H-pyrazolo[4,3-c]cinnolin-3-one, 2,5-dihydro-7,8-methylenedioxy-2-phenyl-3H-pyrazolo[4,3-c]cinnolin-3-one and their non-toxic, pharmaceutically acceptable acid addition salts.

The novel process of the invention for the preparation of the compounds of formula I comprises reacting a compound of the formula

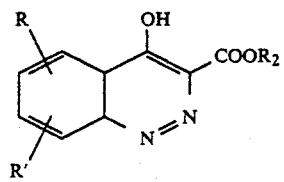

II wherein R and R' have the above definitions and R$_2$ is linear alkyl of 1 to 5 carbon atoms with a chlorinating agent to obtain a compound of the formula

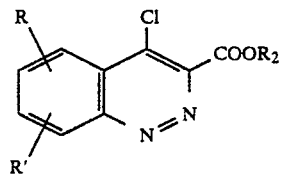

III and reacting the latter with a hydrazine compound of the formula

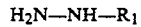

IV wherein R$_1$ has the above definition to obtain the corresponding compound of formula I which may be salified to form the acid addition salt.

The chlorinating agent may be phosphorous oxychloride, oxalyl chloride and preferably thionyl chloride and the reaction is preferably effected at reflux in an organic solvent such as benzene, toluene, xylene or dimethylformamide. The reaction of the compounds of formulae III and IV is preferably effected at reflux in an organic solvent such as xylene, dimethylformamide and preferably anisole.

The salification of the compounds of formula I may be effected by reacting substantially stoichiometric amounts of the compound of formula I, with or without isolation, and the desired acid.

The starting compounds of formula II are known or can be prepared by known processes such as described in *J. Chem. Soc.*, (1961), p. 2828 and *J. Chem. Soc.*, Suppl. I. (1964), p. 5659. The compounds of formula IV are known or can be made by known processes such as *Liebigs Ann. der. Chem.* (1931) 486, p. 95 or *J. Chem. Soc.*, (1959), p. 3830-3834.

The novel anxiolytic compositions of the invention are comprised of an anxiolytically effective amount of at least one compound of formula I and their non-toxic, pharmaceutically acceptable acid addition salts and a pharmaceutical carrier or excipient. The compositions may be in the form of tablets, dragees, gelules, granules, suppositories or injectable solution or suspensions.

Examples of suitable excipients are talc, gun arabic, lactose, starch, magnesium stearate, cocoa butter, aqueous and non-aqueous vehicles, animal or vegetable fatty substances, paraffin derivatives, glycols, diverse wetting agents, dispersants or emulsifiers and preservatives.

The anxiolytic compositions are useful for the treatment of anxiety conditions such as chronic anxiety optionally associated with insomnia or behavioral problems, distress in adults or children or to complement treatment with neuroleptics or antidepressants of psychotic or depressive conditions.

Examples of preferred active ingredients in the components are compounds of formula I wherein R is hydrogen, halogen, alkyl and alkoxy of 1 to 5 carbon atoms, $-NO_2$ or $-CF_3$, those wherein R' is hydrogen, those wherein $R_1$ is phenyl optionally substituted with alkyl or alkoxy of 1 to 5 carbon atoms or halogen or pyridyl or thiazolyl and their non-toxic, pharmaceutically acceptable acid addition salts. More preferably R is in the 8-position and $R_1$ is phenyl and their acid addition salts.

Especially preferred are 8-chloro-2,5-dihydro-2-phenyl-3H-pyrazolo[4,3-c]cinnolin-3-one, 2,5-dihydro-2-phenyl-3H-pyrazolo[4,3-c]cinnolin-3-one and 2,5-dihydro-2-pyrid-2-yl-3H-pyrazolo-[4,3-c]cinnolin-3-one and their non-toxic, pharmaceutically acceptable acid addition salts.

The novel method of the invention for treating anxiety in warm-blooded animals, including humans, comprises administering to warm-blooded animals an anxiolytically effective amount of at least one compound of formula I and their non-toxic, pharmaceutically acceptable acid addition salts. The compounds may be administered orally, rectally or parentically. The usual daily dose is 0.01 to 7 mg/kg depending on the compound used, the method of administration and the condition treated. For example, the daily oral dose for treatment of humans for chronic anxiety with the compound of Example 1 is 0.03 to 3 mg/kg.

The novel intermediates of the invention are the compounds of formula III.

In the following examples there are described several preferred embodiments to illustrate the invention. However, it is to be understood that the invention is not intended to be limited to the specific embodiments.

EXAMPLE 1

8-chloro-2,5-dihydro-2-phenyl-3H-pyrazolo[4,3-c]cinnolin-3-one

STEP A: Ethyl 4,6-dichloro-3-cinnolin carboxylate

A solution of 6 g of ethyl 6-chloro-4-hydroxy-3-cinnolin carboxylate in 300 cm$^3$ of thionyl chloride and 1 cm$^3$ of dimethyl formamide was stirred for 16 hours at reflux and the thionyl chloride was concentrated under reduced pressure. The residue was taken up several times in 50 ml of toluene to obtain 6 g of ethyl 4,6-dichloro-3-cinnolin carboxylate as a greenish residue melting at $\approx 50°$ C.

STEP B: 8-chloro-2,5-dihydro-2-phenyl-3H-pyrazolo[4,3-c]cinnolin-3-one

In an inert atmosphere, 6 g of the product of Step A were mixed with 60 ml of anisole and the insoluble matter was removed by filtering. 2.4 ml of phenyl hydrazine were added to the filtrate and the mixture was placed in a water bath at 150° C. for 2½ hours. The mixture was cooled, dried, washed with ethyl acetate and evaporated to dryness. The residue was washed with an aqueous solution of N hydrochloric acid and was dissolved in a solution of 25 ml of concentrated ammonia and 75 ml water. The solution was filtered and the aqueous phase was extracted with ether. Sodium phosphate was added and the product was purified by triturating in ethanol, then in water. The product was dried to obtain 2.22 g of 8-chloro-2,5-dihydro-2-phenyl-3H-pyrazolo[4,3-c]cinnolin-3-one melting at >280° C.

Analysis: $C_{15}H_9Cl\ N_4O$ molecular weight=296.78.
Calculated: %C 60.71; %H 3.05; %N 18.88; %Cl 11.94.
Found: %C 60.4; %H 3.1; %N 18.8; %Cl 11.8.

EXAMPLES 2 to 10

Using the procedure of Example 1, the following products were prepared and their melting points and analysis are reported in the following Table.

Example 2: 2-(4-chlorophenyl)-2,5-dihydro-3H-pyrazolo[4,3-c]cinnolin-3-one.

Example 3: 2,5-dihydro-2-phenyl-3H-pyrazolo[4,3-c]cinnolin-3-one.

Example 4: 2,5-dihydro-2-(4-methoxyphenyl)-3H-pyrazolo[4,3-c]cinnolin-3-one.

Example 5: 2,5-dihydro-2-(4-benzyloxyphenyl)-3H-pyrazolo[4,3-c]cinnolin-3-one.

Example 6: 2,5-dihydro-2-(3-trifluoromethylphenyl)-3H-pyrazolo[4,3-c]cinnolin-3-one.

Example 7: 2,5-dihydro-2-(2-methylphenyl)-3H-pyrazolo[4,3-c]cinnolin-3-one.

Example 8: 2,5-dihydro-(2-pyridin-2-yl)-3H-pyrazolo[4,3-c]cinnolin-3-one hydrochloride.

Example 9: 2,5-dihydro-(2-thiazol-2-yl)-3H-pyrazolo[4,3-c]cinnolin-3-one hydrochloride.

Example 10: 2,5-dihydro-(2-dihydrothiazol-2-yl)-3H-pyrazolo[4,3-c]cinnolin-3-one hydrochloride.

PREPARATION OF ETHYL 4-CHLORO-3-CINNOLIN CARBOXYLATE

A solution of 4 g of ethyl-4-hydroxy-3-cinnolin carboxylate in 250 ml of thionyl chloride was agitated at reflux for 16 hours and then thionyl chloride was concentrated under reduced pressure. The residue was taken up 3 times in 50 ml of toluene to obtain 4 g of a greenish residual oil which was ethyl 4-chloro-3-cinnolin carboxylate.

| Example | Salt | R | R' | R₁ | Crystallization solvent | m.p. in °C. | Crude Formula | Molecular weight | Microanalysis Calculated Found | | | | |
|---|---|---|---|---|---|---|---|---|---|---|---|---|---|
| | | | | | | | | | C % | H % | N % | Cl % | S % |
| 1 | | 8-Cl | H | 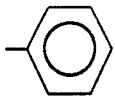 | naught | >280° C. | $C_{15}H_9ClN_4O$ | 296,718 | 60,71<br>60,4 | 3,05<br>3,1 | 18,88<br>18,8 | 11,94<br>11,78 | |
| 2 | | H | H | 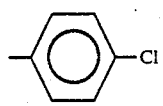 | naught | >280° C. | $C_{15}H_9ClN_4O$ | 296,718 | 60,71<br>60,6 | 3,05<br>3,0 | 18,88<br>18,8 | 11,94<br>12,1 | |
| 3 | | H | H | 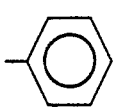 | naught | >280° C. | $C_{15}H_{10}N_4O$ | 262,273 | 68,69<br>68,2 | 3,84<br>3,8 | 21,36<br>21,1 | | |
| 4 | | H | H | 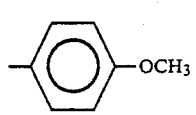 | MeOH | >280° C. | $C_{16}H_{12}N_4O_2$ | 292,30 | 65,74<br>65,5 | 4,13<br>4,1 | 19,16<br>19,0 | | |
| 5 | | H | H | 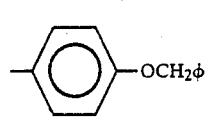 | Isopropanol | >260° C. | $C_{22}H_{16}N_4O_2$ | 368,39 | 71,72<br>71,4 | 4,37<br>4,3 | 15,2<br>14,9 | | |
| | | | | | | | | | | | | F % | |
| 6 | | H | H | 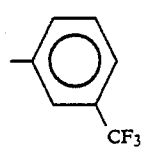 | naught | >260° C. | $C_{16}H_9N_4F_3O$ | 330,27 | 58,18<br>57,8 | 2,74<br>2,7 | 16,96<br>16,8 | 17,25<br>17,00 | |
| 7 | | H | H | 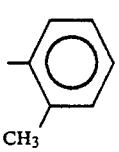 | propanol | >280° C. | $C_{16}H_{12}N_4O$ | 276,30 | 69,55<br>68,85 | 4,37<br>4,32 | 20,27<br>20,0 | | |
| | | | | | | | | | | | | Cl % | |
| 8 | HCl | H | H | 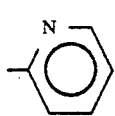 | propanol | >280° C. | $C_{14}H_{10}N_5ClO$ | 299,72 | 56,10<br>55,9 | 3,36<br>3,3 | 23,36<br>23,3 | 11,82<br>11,9 | — <br>— |
| 9 | | H | H | 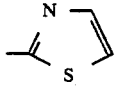 | MeOH | >280° C. | $C_{12}H_7N_5SO$ | 269,286 | 53,52<br>53,1 | 2,62<br>2,6 | 26,00<br>25,6 | —<br>— | 11,90<br>11,78 |
| 10 | HCl | H | H | 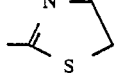 | naught | >280° C. | $C_{12}H_{10}N_6SOCl$ | 307,763 | 46,83<br>47,0 | 3,27<br>3,3 | 22,75<br>22,8 | 11,51<br>10,6 | 10,41<br>10,2 |

EXAMPLE 11

Tablets were prepared containing 10 mg of 8-chloro-2,5-dihydro-2-phenyl-3H-pyrazolo[4,3-c]cinnolin-3-one or 2,5-dihydro-2-phenyl-3H-pyrazolo[4,3-c]cinnolin-3-one or 2,5-dihydro-2-(pyridin-2-yl)-3H-pyrazolo[4,3-c]cinnolin-3-one hydrochloride and sufficient excipient of lactose, starch, talc and magnesium stearate for a final tablet weight of 100 mg.

PHARMACOLOGICAL DATA

A. Affinity for benzodiazepine receptors

The cortices removed from the brains of male rats weighing an average of 150 g were homogenized to one twentieth part (weight/volume) in 0.32M sucrose. After centrifuging the homogenate at 1000 g for 10 minutes at 0° C., the supernatant layer was centrifuged at 30,000 g for 20 minutes at +4° C. The residue was suspended in 20 volumes of Tris HCl 50 mM buffer with a pH of 7.4 and centrifuged at 30,000 g for 20 minutes at +4° C. The new residue obtained was suspended in 50 ml of Krebs Tris HCl buffer, pH 7.4.

2 ml of this suspension in the presence of $^3$H diazepam at a concentration of $10^{-9}$M was incubated for 30 minutes at 0° C., alone, and with increasing concentrations of the product under test, or to determine the non-specific fixation, with non-radio-active diazepam at a concentration of $10^{-6}$M. The incubated suspensions were filtered on Whatman GF/C and the filters were washed twice with 5 ml of Krebs Tris HCl buffer, pH 7.4, at 0° C. The radioactivity of the filters was measured by liquid scintillation. The activity of the product was expressed by CI 50: concentration inhibiting by 50% the specific bonding of $^3$H diazepam, determined graphically.

TABLE I

| Product of the Example | CI 50 in nM |
|---|---|
| 1 | 1.4 |
| 2 | 3.7 |
| 3 | 0.9 |
| 4 | 2.5 |
| 5 | 18 |
| 8 | 3.1 |
| 9 | 3.1 |

B. Staircase test

The apparatus and the method used are described by THIEBOT et al [*Psychol-pharmacologia* (Berlin), 1973, Vol. 31, p. 77]. The experiment was carried out on groups of 15 inexperienced rats and the animals were put individually in the enclosure 1 hour after administration of the compound studied. The number of straightenings up and the number of steps claimed were counted for 3 minutes. At a dose of 20 mg/kg, the product of Example 1 decreased the number of straightenings up by 46% without noticeable modification of the number of steps climbed. Therefore, it has a good anxiety reducing activity.

C. Plate test

The apparatus (Apelab) and the method used are described by BOISSER et al [*European J. Pharmacol.*, 1968, Vol. 4, p. 145]. The plates were linked to a stimulator (U. Sachs, Roucaire) which enabled electric shocks of 120 volts to be delivered during 0.5 seconds. The tests were carried out on groups of 10 mice or rats half an hour after oral administration of the compound studied and each animal has put individually on the apparatus. After 15 seconds of free exploration, it was submitted to an electric shock each time it passed from one plate to another, a minimum of 3 seconds being observed between two shocks. The number of shocks delivered was counted over 1 minute and the results obtained were compared to those observed in the control animals in a test by Dunnett.

At a dose of 20 mg/kg of the product of Example 1, the number of shocks delivered was increased to 63% in mice, and 41% in rats. The increase in the number of shocks was 50% in mice at the dose of 50 mg/kg for the product of Example 3 and at the dose of 100 mg/kg for the product of Example 8. The product of Examples 1, 3 and 8 therefore have a good anxiety reducing activity.

D. Acute toxicity

The lethal dose $LD_0$ of the compound of Example 1 was evaluated after administration orally in mice. The maximum dose not causing any mortality in 8 days was called the $LD_0$. The results are reported in Table II.

TABLE II

| Product of Example | $LD_0$ |
|---|---|
| 1 | >400 |
| 3 | >200 |
| 4 | >400 |
| 5 | >400 |
| 6 | >400 |
| 7 | 200 |
| 8 | >400 |
| 10 | >400 |

Various modifications of the products and process of the invention may be made without departing from the spirit or scope thereof and it should be understood that the invention is intended to be limited only as defined in the appended claims.

What we claim is:

1. A compound selected from the group consisting of pyrazolo[4,3-c]cinnolin-3-one compounds of the formula

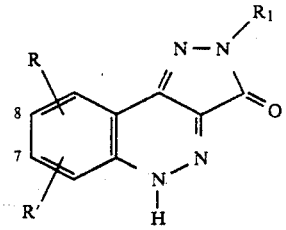

wherein R may be in the 7- or 8-position and is selected from the group consisting of hydrogen, halogen, alkyl and alkoxy of 1 to 5 carbon atoms, $-NO_2$ and $-CF_3$ and R' is hydrogen or R and R' taken together form an alkylenedioxy of 1 to 4 carbon atoms at the 7- or 8-positions and $R_1$ is selected from the group consisting of phenyl, pyridyl, thiazolyl, dihydrothiazolyl and thienyl, all optionally substituted with at least one member of the group consisting of alkyl and alkoxy of 1 to 5 carbon atoms, halogen, mono-, di- and tri- halomethyl and aralkoxy of 7 to 12 carbon atoms and their non-toxic, pharmaceutically acceptable acid addition salts.

2. A compound of claim 1 wherein R' is hydrogen, R is selected from the group consisting of hydrogen, halogen, alkyl and alkoxy of 1 to 5 carbon atoms, $-NO_2$ and $-CF_3$ and $R_1$ is selected from the group consisting of (a) phenyl optionally substituted with alkyl or alkoxy of 1 to 5 carbon atoms or halogen, (b) pyridyl and (c) thiazolyl.

3. A compound of claim 2 wherein R is in the 8-position and $R_1$ is phenyl.

4. A compound of claim 1 selected from the group consisting of 8-chloro-2,5-dihydro-2-phenyl-3H-pyrazolo[4,3-c]cinnolin-3-one and its non-toxic, pharmaceutically acceptable acid addition salts.

5. A compound of claim 1 selected from the group consisting of 2,5-dihydro-2-phenyl-3H-pyrazolo[4,3-c]cinnolin-3-one and its non-toxic, pharmaceutically acceptable acid addition salts.

6. A compound of claim 1 selected from the group consisting of 2,5-dihydro-2-pyrid-2-yl-3H-pyrazolo[4,3- c]cinnolin-3-one and its non-toxic, pharmaceutically acceptable acid addition salts.

7. An anxiolytic composition comprising an anxiolytically effective amount of at least one compound of claim 1 and an inert pharmaceutical carrier.

8. A composition of claim 7 wherein R' is hydrogen, R is selected from the group consisting of hydrogen, halogen, alkyl and alkoxy of 1 to 5 carbon atoms, $-NO_2$ and $-CF_3$ and $R_1$ is selected from the group consisting of (a) phenyl optionally substituted with alkyl or alkoxy of 1 to 5 carbon atoms or halogen, (b) pyridyl and (c) thiazolyl.

9. A compositon of claim 8 wherein R is in the 8-position and $R_1$ is phenyl.

10. A composition of claim 7 wherein the compound is selected from the group consisting of 8-chloro-2,5-dihydro-2-phenyl-3H-pyrazolo[4,3-c]cinnolin-3-one and its non-toxic, pharmaceutically acceptable acid addition salts.

11. A composition of claim 7 wherein the compound is selected from the group consisting of 2,5-dihydro-2-phenyl-3H-pyrazolo[4,3-c]cinnolin-3-one and its non-toxic, pharmaceutically acceptable acid addition salts.

12. A composition of claim 7 wherein the compound is selected from the group consisting of 2,5-dihydro-2-pyrid-2-yl-3H-pyrazolo[4,3-c]cinnolin-3-one and its non-toxic, pharmaceutically acceptable acid addition salts.

13. A method of treating anxiety in warm-blooded animals comprising administering to warm-blooded animals an anxiolytically effective amount of at least one compound of claim 1.

14. A method of claim 13 wherein $R^1$ is hydrogen, R is selected from the group consisting of hydrogen, halogen, alkyl and alkoxy of 1 to 5 carbon atoms, $-NO_2$ and $-CF_3$ and $R_1$ is selected from the group consisting of (a) phenyl optionally substituted with alkyl or alkoxy of 1 to 5 carbon atoms or halogen, (b) pyridyl and (c) thiazolyl.

15. A method of claim 14 wherein R is the 8-position and $R_1$ is phenyl.

16. A method of claim 13 wherein the compound is selected from the group consisting of 8-chloro-2,5-dihydro-2-phenyl-3H-pyrazolo[4,3-c]cinnolin-3-one and its non-toxic, pharmaceutically acceptable acid addition salts.

17. A method of claim 13 wherein the compound is selected from the group consisting of 2,5-dihydro-2-phenyl-3H-pyrazolo[4,3-c]cinnolin-3-one and its non-toxic, pharmaceutically acceptable acid addition salts.

18. A method of claim 13 wherein the compound is selected from the group consisting of 2,5-dihydro-2-pyrid-2-yl-3H-pyrazolo[4,3-c]cinnolin-3-one and its non-toxic, pharmaceutically acceptable acid addition salts.

* * * * *